US006416719B1

(12) United States Patent
Fawcett et al.

(10) Patent No.: US 6,416,719 B1
(45) Date of Patent: Jul. 9, 2002

(54) PLATE LOCATOR FOR PRECISION LIQUID HANDLER

(75) Inventors: Kevin R. Fawcett, Ridgeway; Jeffrey L. Acker, Middleton, both of WI (US)

(73) Assignee: Gilson, Inc., Middleton, WI (US)

(*) Notice: Subject to any disclaimer, the term of this patent is extended or adjusted under 35 U.S.C. 154(b) by 31 days.

(21) Appl. No.: 09/766,136

(22) Filed: Jan. 19, 2001

(51) Int. Cl.⁷ .............................. B01L 3/02; B01L 3/00; B32B 27/04; B32B 27/12; B32B 5/02; G01N 15/06; G01N 33/00; G01N 33/48; A47B 91/00

(52) U.S. Cl. .................. 422/104; 422/99; 422/100; 422/63; 422/68.1; 248/346.03; 248/346.04; 248/678

(58) Field of Search ................... 422/63, 68.1, 67, 422/100, 102, 104, 99; 248/678, 346.03, 346.04

(56) References Cited

U.S. PATENT DOCUMENTS 3,650,306 A * 3/1972 Lancaster
5,227,137 A * 7/1993 Monti et al.
5,770,157 A * 6/1998 Cargill et al.
5,935,859 A * 8/1999 Elliot et al.
5,948,359 A * 9/1999 Kalra et al.
5,962,329 A * 10/1999 Ershov et al.
6,045,760 A * 4/2000 Aizawa et al.
6,103,518 A * 8/2000 Leighton
6,132,582 A * 10/2000 King et al.
6,254,826 B1 * 7/2001 Acosta et al.
2001/0008615 A1 * 7/2001 Little et al.

* cited by examiner

Primary Examiner—Jill Warden
Assistant Examiner—Brian R. Gordon
(74) Attorney, Agent, or Firm—Philip M. Kolehmainen

(57) ABSTRACT

A locator bed has nests where sample well containing plates are held and positioned for accessing by probes moved by an X-Y-Z positioning system. Each nest includes stop posts at two sides of a rectangular base of a plate, and biasing posts at the opposed two sides. The stop posts and the biasing posts have tapered upper guide portions for guiding a descending plate into position and cylindrical lower portions receiving the base of the plate in a seated position. The stop posts are located on the surface of the locator bed by conical seat portions. The biasing posts are placed over studs fastened to the bed surface, and hoop springs are captured between the studs and the biasing posts.

12 Claims, 4 Drawing Sheets

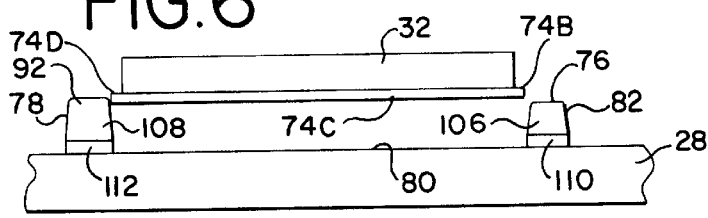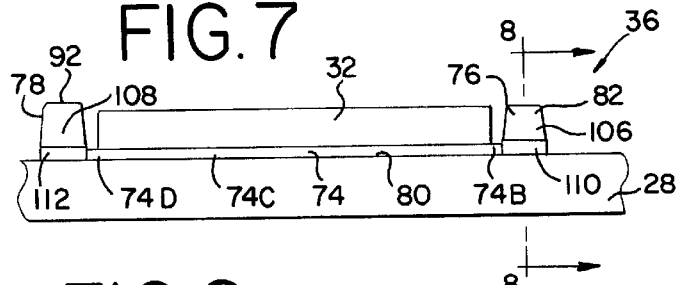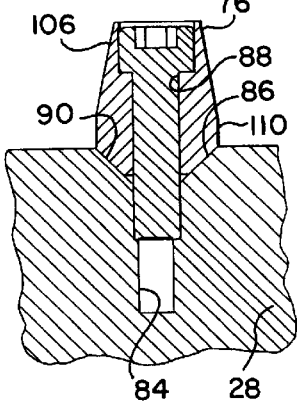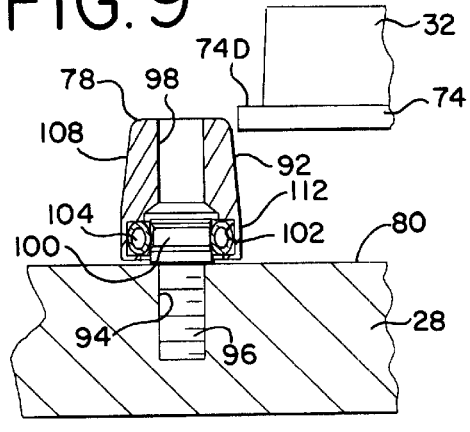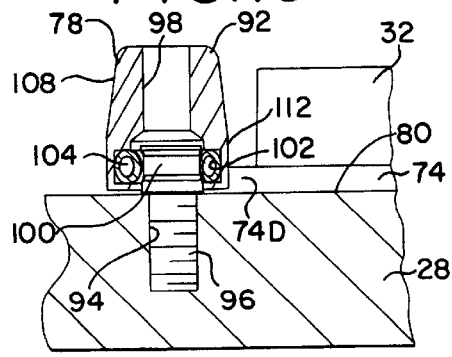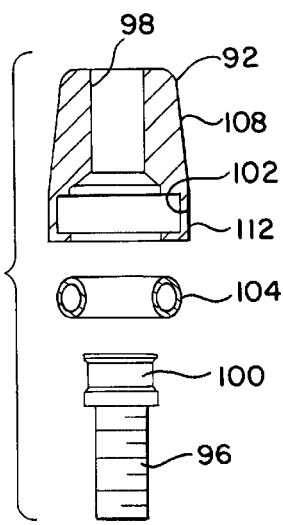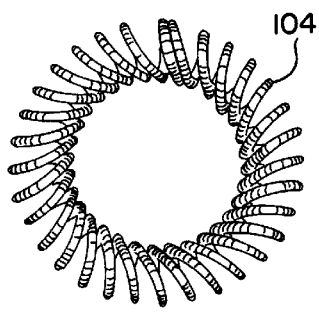

PLATE LOCATOR FOR PRECISION LIQUID HANDLER

FIELD OF THE INVENTION

The present invention relates to precision liquid handlers for pharmaceutical, drug development and similar laboratory applications, and more specifically to a plate locator for holding and accurately positioning sample well plates in a liquid handler.

DESCRIPTION OF THE PRIOR ART

In pharmaceutical, genomic and proteomic research and drug development laboratories, and other biotechnology applications, automated liquid handlers are used for handling laboratory samples in a variety of laboratory procedures. For example, liquid handlers are used for biotechnological and pharmaceutical liquid assay procedures, sample preparation, compound distribution, microarray manufacturing and the like. An automated liquid handler has a work bed that supports an array of sample receptacles. One-piece sample containing plates having an integral array of many sample containing receptacles or wells are widely used. A typical liquid handler has a probe or an array of multiple probes that are moved into alignment with one or more wells to carry out liquid handling operations such as adding liquid to the wells.

It is desirable to decrease the volumes of samples treated with automated liquid handlers. Sample containing plates with a footprint of about three and one-half by five inches and having an X-Y array of 96 wells in an eight by twelve well pattern have been widely used. In order to increase throughput and to reduce consumption of sample constituents, these plates are being superceded by microplates of the same footprint but having an array of smaller wells, for example 384 wells in a sixteen by twenty-four array. This trend is continuing, and there is a need for an automated liquid handler able to accommodate microtiter plates having a very dense array of a very large number of very small volume wells for sample volumes in the nanoliter range. For example, some microtiter plates presently in use have the same footprint as previously used plates but have 1,536 wells in a thirty-two by forty-eight well array.

Microtiter plates with a dense array of small, closely spaced wells present serious problems for an automated liquid handler. In operation, the handler must be precise enough to place every probe of a multiple probe array in exact alignment with a corresponding number of sample containing wells. As well size and spacing decreases, it becomes more difficult for an automated handler to reliably place the liquid handling probes directly over selected sample containing wells.

The margin for error in locating the plates and wells on the work bed of the handler and for positioning the probes relative to the plates and wells decreases as well array density increases. One aspect of the problem is the precise and consistent location of the plates and wells upon the work bed. Approaches such as using manually adjustable clamps or workholders can accurately locate the sample containing plates upon the work surface, but this type of system requires a high degree of operator skill and care, a large number of delicate manual operations and excessive consumption of time in setting up a bed of plates for treatment in the liquid handler. In addition this type of system is not well suited for automated, robotic placement of plates on the bed. It would be desirable to provide a plate locator that is easy and quick to use, that does not require great operator skill, that accommodates robotic placement and that accurately holds and positions sample containing plates on the work bed of a liquid handler.

SUMMARY OF THE INVENTION

A principal object of the present invention is to provide an improved plate locator for positioning and holding sample containing plates on the work bed of a precision liquid handler. Other objects are to provide a plate locator that consistently achieves precise plate positioning; that is easy to use and does not require great care or skill to locate plates on the work bed; that is suited to robotic placement of plates on the work bed; and that is simple and inexpensive yet reliable and rugged.

In brief, in accordance with the invention there is provided a plate locator for positioning and holding a four sided plate having an array of sample containing wells, such as a microplate, on a work bed of a precision liquid handler having at least one probe for registration with at least one well of the plate. The plate locator apparatus includes a flat, planar locator bed adapted to be secured to the work bed of the precision liquid handler. A plate receiving nest on the locator bed has four sides corresponding to the four sides of the four sided plate. The nest includes rigid stop members extending up from the bed on first and second sides of the nest and movably mounted holders extending up from the bed at third and fourth sides of the nest opposite the rigid stop members at the first and second sides of the nest. Resilient biasing elements are connected between the bed and each of the movably mounted holders for urging the holders toward the center of the nest.

BRIEF DESCRIPTION OF THE DRAWINGS

The present invention together with the above and other objects and advantages may best be understood from the following detailed description of the preferred embodiment of the invention illustrated in the drawings, wherein:

FIG. 6 is a side view taken from the line 6—6 of FIG. 3 showing a plate and portions of a nest with the plate positioned above the nest;

FIG. 7 is a view like FIG. 6 showing the plate in place in the nests;

FIG. 8 is an enlarged sectional view of a rigid stop member of the nest, taken along he line 8—8 of FIG. 7;

FIG. 9 is an enlarged, fragmentary, sectional view taken along the line 9—9 of FIG. 3, showing the nest and plate in the positions of FIG. 6 with the plate positioned above the nest;

FIG. 10 is a view like FIG. 9 showing the plate in place in the nests;

FIG. 11 is an exploded sectional view of a movable holder of the nests; and

FIG. 12 is an enlarged top plan view of a hoop spring of a movable holder of the nest.

DETAILED DESCRIPTION OF THE PREFERRED EMBODIMENTS

Figure 1:
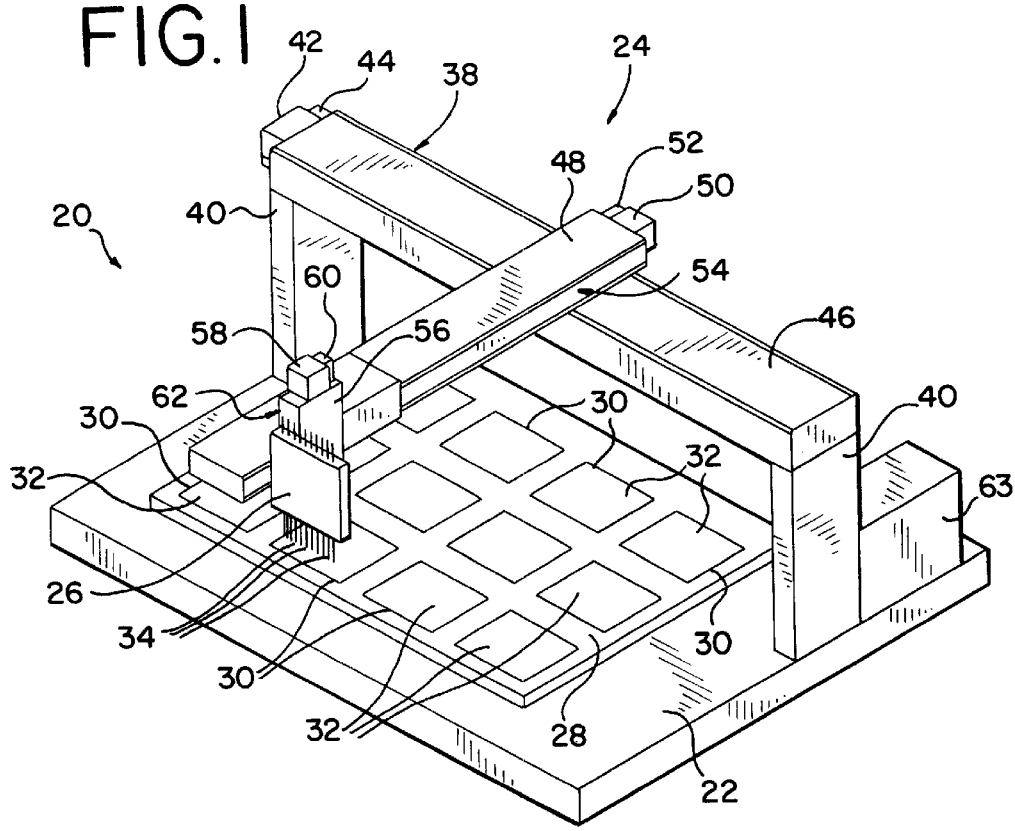
FIG. 1 is a simplified, diagrammatic, isometric view of a precision automated liquid handler with which the plate locator of the present invention is used.

Having reference now to the drawings, and initially to FIG. 1, there is shown in simplified, diagrammatic form an example of an automated precision liquid handler generally designated as 20. The liquid handler 20 includes a table or work bed 22 below an X-Y-Z positioning system 24 carrying a probe holder 26. A locator bed 28 is fixed to the surface of the work bed 22. The locator bed includes a number of nests 30 for holding sample containing plates 32. The probe holder 26 supports individual probes 34 that are moved by the positioning system 24 to predetermined locations above the plates 32. As described below, each of the nests 30 includes a plate locator apparatus generally designated as 36 and constructed in accordance with the principles of the present invention.

The X-Y-Z positioning system 24 moves the probe holder 26 above the work bed 22 and positions it with great precision in predetermined positions relative to the work bed 22. The system 24 includes an X drive assembly 38 mounted above and to the rear of the work bed 22 by suitable supports 40. An X drive motor 42, with an encoder 44, operates a mechanism within an X arm 46 to move a Y arm 48 from side to side in the X direction. A Y drive motor 50, with an encoder 52, of a Y drive assembly 54 operates a mechanism within the Y arm 48 to move a Z arm 56 forward and back in the Y direction. A Z drive motor 58, with an encoder 60, of a Z drive assembly 62 operates a mechanism within the Z arm 56 to move the probe holder 26 up and down in the Z direction. A programmable controller 63 is connected by cables (not shown) to the motors 42, 50 and 58 and to the encoders 44, 52 and 60. Controller 63 may include a microprocessor based operating system capable of controlling the motion of the probe holder 26 in accordance with programmed instructions saved in memory of the controller and/or communicated to the controller from a remote source. Linear encoders may be used in place of the illustrated encoders 44, 52 and 60.

Figure 2:
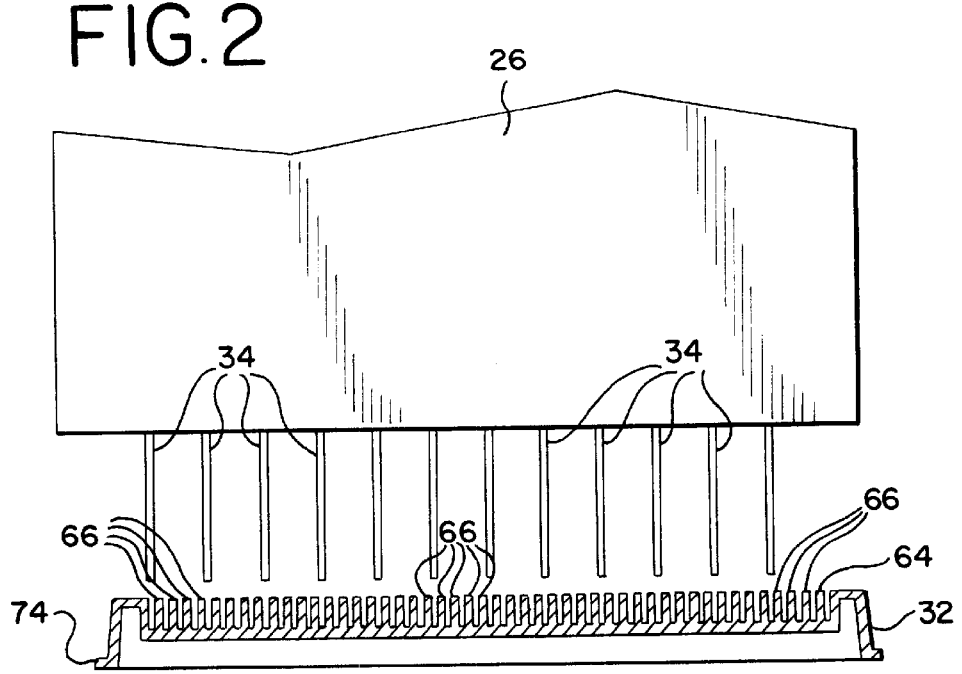
FIG. 2 is an enlarged, fragmentary front view of the probe carrier and multiple probes of the precision liquid handler of FIG. 1, showing the probes in registration with wells of a microplate.

Each plate locator apparatus 36 positions and holds upon the work bed 22 a plate 32 including an array of many individual sample containing wells. The plate 32 has a footprint of about three and one-half by five inches, and known plates may have an X-Y array of 96 wells in an eight by twelve well pattern, or an array of 384 smaller wells in a sixteen by twenty-four array, or an array of 1,536 nanoliter volume wells in a thirty-two by forty-eight well pattern. A cross sectional view of a plate 32 of this latter configuration is seen in FIG. 2, along with the probe holder 26 carrying twelve individual probes 34. This plate 32 includes thirty-two rows 64 each having forty-eight sample wells 66, one row 64 being seen in FIG. 2. Each well 66 has a width of 1.2 millimeters and the center to center well spacing is 2.25 millimeters. The diameter of each probe 34 is 1.1 millimeters, and the center to center probe spacing is nine millimeters, or five wells.

Each probe 34 can discharge liquid in a droplet size of 0.2 millimeter. The probe holder 26 is moved to the location seen in FIG. 2 to distribute liquid to the twelve wells 66 that are aligned under the probes 34. The probe holder 26 is then moved by the X-Y-Z positioning system 24 to align the probes 34 with another set of wells 66. In this manner some or all of the wells 66 of the plate 32, and of some or all of the plates 32, can be supplied with liquid. Because of the small well size and spacing, and the small probe size and spacing, great precision is required. In order for the X-Y-Z positioning system to align the probes 34 with wells 66, the positions of the wells 66 and thus the positions of the plates 32 must be precisely determined. This is the result achieved by the plate locator 36 of the present invention.

Figure 3:
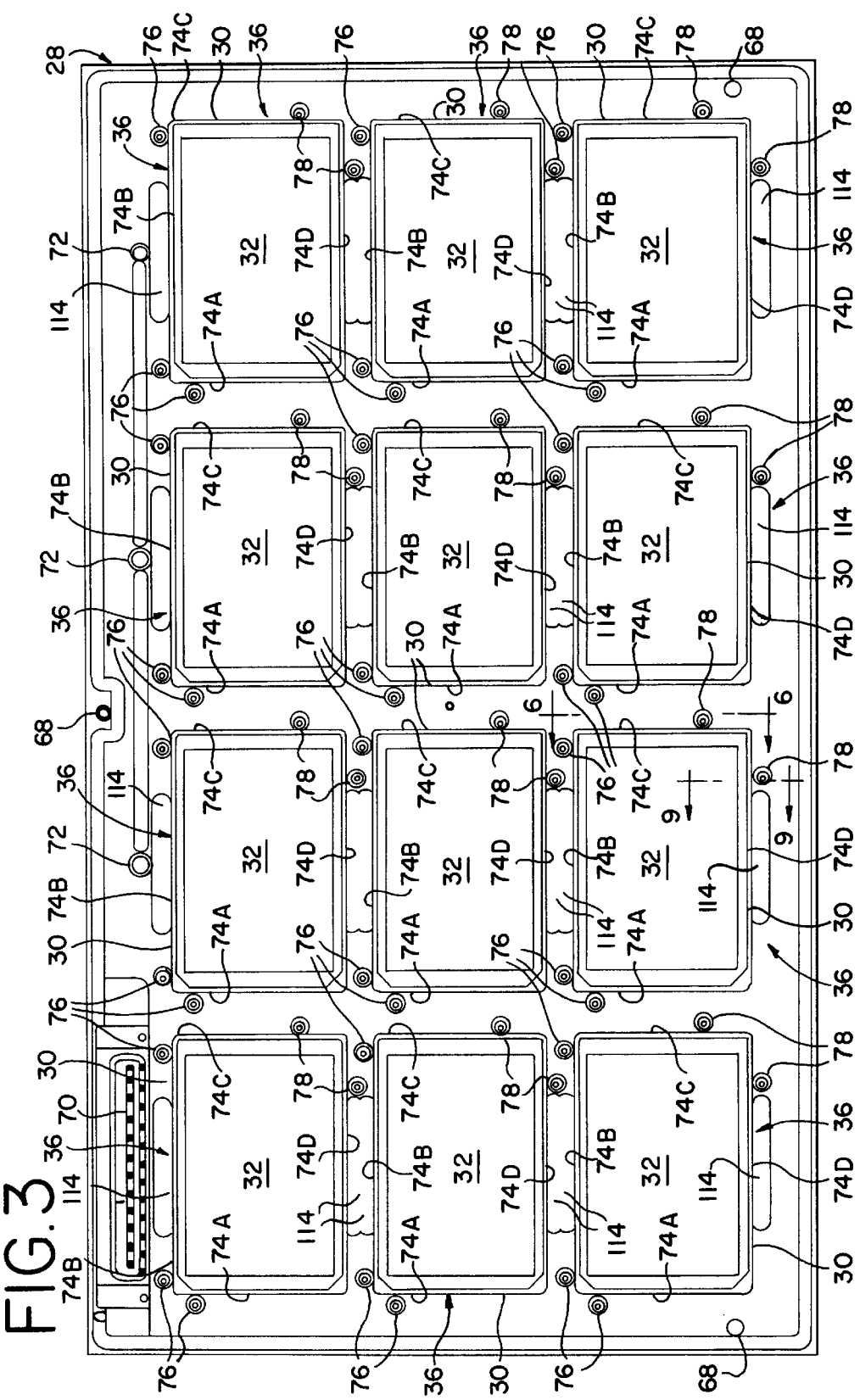
FIG. 3 is a top plan view of the work bed of the precision automated liquid handler of FIG. 1, including an array of plate nests, each having a plate locator constructed in accordance with the present invention.

FIG. 3 shows the locator bed 28, preferably a thick, stable panel of metal such as aluminum fastened to the work bed 22 of the liquid handler 20 at three leveling and locating points 68 so that the location of the locator bed 28 can be precisely adjusted and fixed on the work bed 22. The locator bed 28 includes a probe rinse station 70 and probe locator sockets or tubes 72 that can be used to assess the probe locations for initializing the operation of the positioning system 24. The locator bed 28 also includes an array of twelve tray nests 30 in a three by four nest pattern. Each nest 30 includes a plate locator apparatus 36 holding a plate 32. Each plate 32 may be a 1,536 microtiter plate such as seen in FIG. 2, or may be of another configuration. Regardless of well size and configuration, each plate has a four sided base 74 of a consistent, known size and shape.

Figure 4:
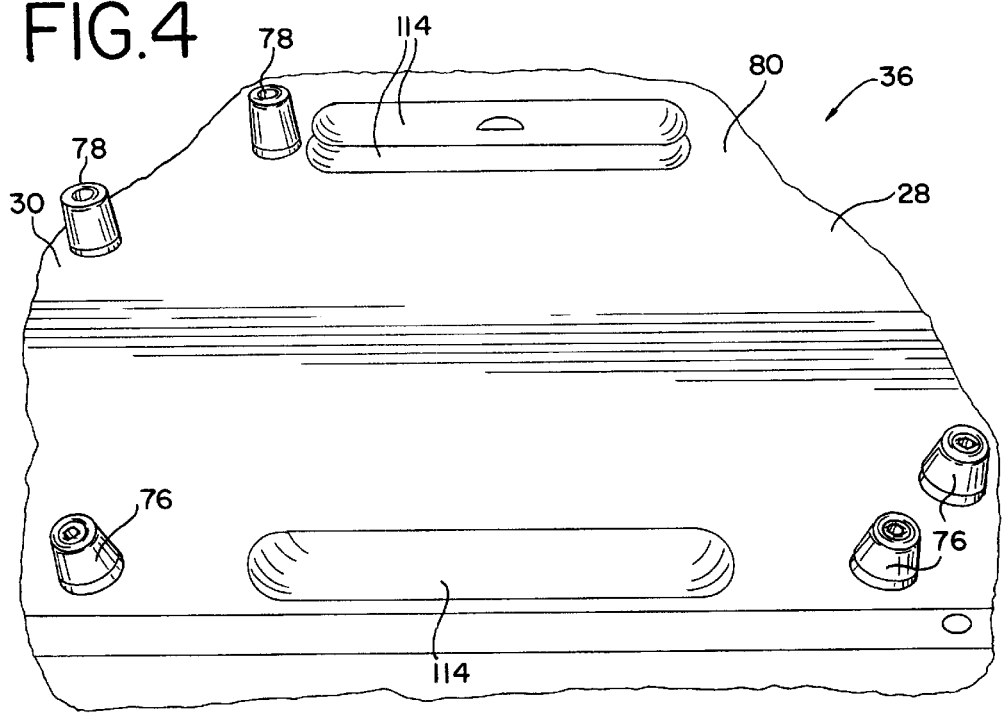
FIG. 4 is a rear and top perspective view of one of the plate nests of the work bed of FIG. 3, showing the nest empty and before a plate is placed into the nest.
Figure 5:
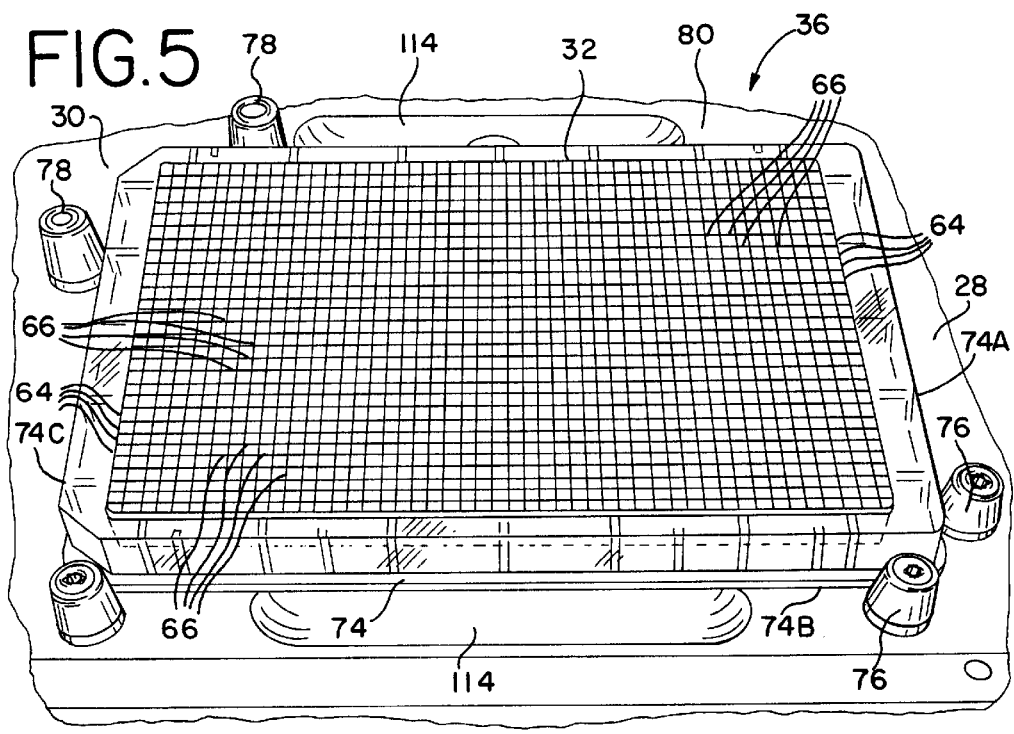
FIG. 5 is a view like FIG. 4 showing the nest with a plate in place.

A nest 30 with its plate locator apparatus 36 is seen in more detail in FIGS. 4 and 5. The plate locator apparatus 36 includes rigid stop members 76 engageable with two sides 74A and 74B of the four sided tray base 74 and movable holders 78 at the remaining two sides 74C and 74D. When a plate 32 is placed into the nest 30, the movable holders 78 are contacted by the sides 74C and 74D and are displaced outwardly to permit downward movement of the base 74 until it rests upon the top surface 80 of the locator bed 28. In this seated position, the sides 74A and 74B are in engagement with the rigid stop members 76. The rigid stop members 76 are fixed to the locator bed 28 in a known position, and the rigid stop members 76 determine the position of the plate 32 because they contact two sides of the base 74. As a result, when the plate 32 is seated in the nest 30, it is in a precisely fixed and known position and the wells 66 can reliably be accessed by the positioning system 24 and the probes 34.

The rigid stop members 76 are stop posts 82. One is shown in detail in FIG. 8. A threaded opening 84 is made in the top surface 80 at a precisely determined position. The opening 84 has a conical upper portion 86. The post 82 has a central opening 88 and a conical base 90 matching the shape of the opening portion 86. Base 90 is seated in the opening portion 86 and this locates the post 82 on the surface 80. A cap screw received in the opening 88 is threaded into the opening 88 to attach the post 82 in place. The post 82 is symmetrical about its central axis, with a circular cross section throughout its length, and can be mounted in any rotational position.

The movable holders 78 are biasing posts 92 and are seen in detail in FIGS. 9–11. For each post 92, a threaded opening 94 is made in the top surface 80 at a precise location. A stud 96 is threaded into the opening, and the biasing post 92 is placed over the stud 96 with the stud 96 received in a central opening 98 in the post 92. The stud 96 and the post 92 are symmetrical about their central axes, with circular cross sections throughout their lengths, and can be installed in any rotational position.

Interfacing channels 100 and 102 in the stud 96 and in the interior of the post 92 define a spring chamber containing a hoop spring 104. The hoop spring 104 is a wire wound coil spring having an annular shape similar to that of the spring receiving chamber, with individual windings surrounding the circular spring axis. The hoop spring 104 resiliently biases the post 92 to a central position wherein the axes of the stud 96 and post 92 coincide, and permits the post 92 to be displaced laterally from this central position while maintain a restoring return force on the post 92.

FIG. 6 illustrates a plate 32 as it enters the nest 30. The stop post 82 has an inclined, tapered upper portion 106, and the post 92 has an inclined, tapered upper portion 108. The surfaces 106 and 108 receive and guide the base 74 of the plate 32 as it moves downward toward the surface 80. The surface 108 acts as a cam, and the descending base 74 forces the bias post 92 outwardly against the force of the hoop spring 104. The stop post 82 has a cylindrical lower portion 110 immediately adjacent to the surface 80, and the bias post 92 has a cylindrical lower portion 112 immediately adjacent to the surface 80. As the base 74 reaches its home position against the surface 80, the edges of the base (i.e. the edges 74B and 74D in FIG. 7) contact these cylindrical surfaces 110 and 112 and there is no tendency for the base to be lifted away from the surface 80.

In the initial position of the posts 82 and 92, the spacing between the cylindrical portions 110 and 112 is slightly less than the width of length of the base 74 of the plate 32. In the fully nested, home position of the plate 32, as can be seen from comparing FIGS. 9 and 10, the hoop spring 104 is compressed at the region of a radial line extending through the point of contact of the biasing post 92 with the base 74. The resulting resilient force applied by the biasing post 92 against the base 74 holds the base 74 firmly against the stop post or posts 82 on the opposite side of the base 74. Therefore the system of stop posts 82 and biasing posts 92 guides the descending plate 32 into place and also precisely determines the nested position of the plate 32.

Each nest 30 includes three stop posts 82 and two biasing posts 92 (FIGS. 3–5). Two stop posts 82 are located near opposite ends of one of the longer sides 74B of the base 74. A third stop post is located at an adjacent side 74A near the corner with side 74B. These three posts define an unambiguous, certain position for a plate 32 held in the nest. No rotation or deviation of the plate 32 from the intended position can occur when the base 74 contacts the three stop posts 82. The two biasing posts 92 are located on the two sides 74C and 74D opposite the sides 74A and 74D engaged by the stop posts 82. These two biasing posts 92 apply forces in two perpendicular directions to force the base 74 firmly against the three stop posts 82. This provides a simple arrangement that is inexpensive to fabricate and assemble.

No special skill or care is needed to place a plate 32 into the nest where is it held in a precise, known position. In addition, the plate can be removed with a simple lifting motion because the plate is not latched or locked in place by any structure engaging a top surface of the plate. The plate locator apparatus 36 of the present invention is well suited for robotic plate placement and removal because the final positioning of the plate is carried out by the plate locator 36 associated with the locator bed 28 and not by the person or machine that places the tray onto the surface 80. To facilitate robotic placement and removal, each nest 30 includes opposed recesses 114 in the surface 80 at opposite sides of the nest. The recesses 114 provide clearance for gripping the edges of the base 74.

While the present invention has been described with reference to the details of the embodiment of the invention shown in the drawing, these details are not intended to limit the scope of the invention as claimed in the appended claims.

What is claimed is:

1. A plate locator for positioning and holding a four sided plate having an array of sample containing wells, such as a microplate, on a work bed of a precision liquid handler having at least one probe for registration with at least one well of the plate, said plate locator apparatus comprising:

a flat, planar locator bed adapted to be secured to the work bed of the precision liquid handler;

a plate receiving nest on said locator bed, said nest having four sides corresponding to the four sides of the four sided plate;

said nest including rigid stop members extending up from said bed on first and second sides of said nest;

said nest including movably mounted holders extending up from said bed at third and fourth sides of said nest opposite said rigid stop members at said first and second sides of said nest; and resilient biasing elements connected between said bed and each of said movably mounted holders for urging said holders toward the center of said nest.

2. The plate locator of claim 1, wherein there are only three said rigid stop members and only two said movably mounted holders.

3. The plate locator of claim 2, said two movably mounted holders being located near a first corner where said third and fourth sides intersect, and two of said three rigid stop member being located near a second corner opposite said first corner.

4. The plate locator of claim 1, further comprising access recesses in said bed adjacent an opposed pair of sides of said nest.

5. The plate locator of claim 1, said rigid stop members comprising stop posts.

6. The plate locator of claim 5, said bed having a conical recess for each of said stop posts, said stop posts being circular in cross section throughout their lengths and each having a conical bottom portion received in a corresponding said conical recess.

7. The plate locator of claim 1, each of said movably mounted holders comprising a biasing post.

8. The plate locator of claim 7, further comprising a stud secured to said bed for each said biasing post, said biasing post having a central cavity receiving said stud.

9. The plate locator of claim 8, said resilient biasing element comprising a spring in said cavity between said stud and said biasing post.

10. The plate locator of claim 9, said stud and said biasing post having circular cross sections and defining an annular spring receiving chamber between said stud and biasing post in said cavity, said spring being received in said annular chamber.

11. The plate locator of claim 10, said spring comprising a hoop spring having coils surrounding a circular axis.

12. The plate locator of claim 1, said rigid stop members and said movably mounted holders comprising posts having vertical portions immediately adjacent said bed and having inclined plate guide portions above said vertical portions.

* * * * *